US00PP18394P2

(12) United States Plant Patent
Head et al.

(10) Patent No.: US PP18,394 P2
(45) Date of Patent: Jan. 1, 2008

(54) ***CAMPSIS* PLANT NAMED 'HOMR'**

(50) Latin Name: *Campsis×tagliabuana*
Varietal Denomination: HOMR

(75) Inventors: Robert Harold Head, Seneca, SC (US); Lisa Jones Head, Seneca, SC (US); William A. Head, Walhalla, SC (US)

(73) Assignee: Head Ornamentals, Inc., Seneca, SC (US)

( * ) Notice: Subject to any disclaimer, the term of this patent is extended or adjusted under 35 U.S.C. 154(b) by 0 days.

(21) Appl. No.: 11/513,613

(22) Filed: Aug. 31, 2006

(51) Int. Cl.
*A01H 5/00* (2006.01)

(52) U.S. Cl. ..... Plt./226
(58) Field of Classification Search ..... Plt./226
See application file for complete search history.

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Campsis* plant named 'HOMR', characterized by its compact and vining growth habit; leaves, and stems with dense pubescence; freely flowering plant habit; long flowering period; large red-colored flowers arranged in large panicles; and good garden performance.

2 Drawing Sheets

Botanical designation: *Campsis×tagliabuana.*
Cultivar denomination: 'HOMR'.

BACKGROUND OF THE INVENTION

The present invention relates to a new and distinct cultivar of *Campsis,* botanically known as *Campsis×tagliabuana* and hereinafter referred to by the name 'HOMR'.

The new *Campsis* is a product of a planned breeding program conducted by the Inventors in Seneca, S.C. The objective of the breeding program is to create new *Campsis* cultivars with attractive plant form and flower coloration.

The new *Campsis* originated from a self-pollination made by the Inventors in 1990, in Seneca, S.C. of the *Campsis×tagliabuana* cultivar Madame Galen, not patented. The new *Campsis* was discovered and selected by the Inventor as a single flowering plant within the progeny of the stated self-pollination in a controlled environment in Seneca, S.C. in 1993.

Asexual reproduction of the new *Campsis* by terminal cuttings in a controlled environment in Seneca, S.C. since August, 1995, has shown that the unique features of this new *Campsis* are stable and reproduced true to type in successive generations.

SUMMARY OF THE INVENTION

The cultivar HOMR has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'HOMR'. These characteristics in combination distinguish 'HOMR' as a new and distinct cultivar of *Campsis:*

1. Compact and vining growth habit.
2. Leaves and stems with dense pubescence.
3. Freely flowering plant habit.

4. Long flowering period.
5. Large red-colored flowers arranged in large panicles.
6. Good garden performance.

Plants of the new *Campsis* can be compared to plants of the parent, the cultivar Madame Galen. Plants of the new *Campsis* differ from plants of the cultivar Madame Galen in the following characteristics:

1. Plants of the new *Campsis* are not as spreading as and slower growing than plants of the cultivar Madame Galen.
2. Leaves of plants of the new *Campsis* are pubescent whereas leaves of plants of the cultivar Madame Galen are glabrous.
3. Plants of the new *Campsis* flower more freely and for a longer period of time than plants of the cultivar Madame Galen.
4. Plants of the new *Campsis* have larger flowers than plants of the cultivar Madame Galen.
5. Plants of the new *Campsis* rarely produce fruit whereas plants of the cultivar Madame Galen produce numerous fruits.

Plants of the new *Campsis* can be compared to plants of the cultivar Kudian, disclosed in U.S. Plant Pat. No. 13,139. In side-by-side comparisons conducted in Seneca, S.C., plants of the new *Campsis* differed from plants of the cultivar Kudian in the following characteristics:

1. Plants of the new *Campsis* were more upright than and not as outwardly spreading as plants of the cultivar Kudian.
2. Plants of the new *Campsis* had shorter internodes than plants of the cultivar Kudian.
3. Upper leaf surfaces of plants of the new *Campsis* were pubescent whereas upper leaf surfaces of plants of the cultivar Kudian were glabrous.
4. Plants of the new *Campsis* flowered earlier and more freely than plants of the cultivar Kudian.
5. Plants of the new *Campsis* had larger flowers than plants of the cultivar Kudian.

6. Flower color of plants of the new *Campsis* was red whereas flower color of plants of the cultivar Kudian was orange red.
7. Plants of the new *Campsis* rarely produced fruit whereas plants of the cultivar Kudain produced numerous fruits.

Plants of the new *Campsis* can be also compared to plants of the cultivar Crimson Trumpet, not patented. In side-by-side comparisons conducted in Seneca, S.C., plants of the new *Campsis* differed from plants of the cultivar Crimson Trumpet in the following characteristics:

1. Plants of the new *Campsis* were more compact than plants of the cultivar Crimson Trumpet.
2. Leaves of plants of the new *Campsis* were pubescent whereas leaves of plants of the cultivar Crimson Trumpet were glabrous.
3. Plants of the new *Campsis* flowered earlier than plants of the cultivar Crimson Trumpet.
4. Flower color of plants of the new *Campsis* was red whereas flower color of plants of the cultivar Crimson Trumpet was dark red.
5. Plants of the new *Campsis* rarely produced fruit whereas plants of the cultivar Crimson Trumpet produced numerous fruits.

BRIEF DESCRIPTION OF THE PHOTOGRAPHS

The accompanying colored photographs illustrate the overall appearance of the new *Campsis,* showing the colors as true as it is reasonably possible to obtain in colored reproductions of this type. Colors in the photographs may differ slightly from the color values cited in the detailed botanical description which accurately describe the colors of the new *Campsis.*

The photograph on the first sheet comprises a side perspective view of typical flowering plants of 'HOMR' grown in containers.

The photograph on the second sheet comprises a close-up of typical flowers of 'HOMR'.

DETAILED BOTANICAL DESCRIPTION

The photographs and following observations, measurements and values describe plants grown in Seneca, S.C., under commercial practice in an outdoor nursery in two-gallon containers. During the production of the plants, day temperatures ranging from −5° C. to 40° C. and night temperatures ranging from −22° C. to 35° C. Plants were grown for about eight months when the photographs and description were taken. In the following description, color references are made to The Royal Horticultural Society Colour Chart, 1995 Edition, except where general terms of ordinary dictionary significance are used.

Botanical classification: *Campsis×tagliabuana* cultivar HOMR.

Parentage: Self-pollination of *Campsis×tagliabuana* cultivar Madame Galen, not patented.

Propagation:

*Type.*—By softwood stem cuttings.

*Time to initiate roots, summer.*—About 20 days at temperatures of 27° C. to 30° C.

*Time to initiate roots, winter.*—About 30 days at temperatures of 15° C. to 20° C.

*Time to produce a rooted young plant, summer.*—About 40 days at temperatures of 27° C. to 30° C.

*Time to produce a rooted young plant, winter.*—About 60 to 70 days at temperatures of 15° C. to 20° C.

*Root description.*—Primary roots, thick and fleshy; secondary roots, fine and moderately fibrous; 161D in color.

Plant description:

*Plant and growth habit.*—Compact and vining growth habit; stocky and shrubby. Moderate vigorous growth habit.

*Branching habit.*—About one or two basal branches each with about two or three lateral branches.

*Plant height.*—About 50 cm to 100 cm.

*Plant diameter.*—About 35 cm.

Lateral branch description:

*Length.*—About 30 cm to 40 cm.

*Diameter.*—About 5 mm.

*Internode length.*—About 8 cm to 9 cm.

*Strength.*—Strong; stocky.

*Texture.*—Pubescent; velvety.

*Color.*—Young stems, 144A; older stems, 165B.

Foliage description:

*Arrangement.*—Opposite; odd-pinnately compound with 9 to 13 leaflets per leaf.

*Leaflet length.*—About 5 cm to 10 cm.

*Leaflet width.*—About 2.5 cm to 5 cm.

*Leaflet shape.*—Lanceolate.

*Leaflet apex.*—Acute to acuminate.

*Leaflet base.*—Ovate equilateral.

*Leaflet margin.*—Serrate.

*Leaflet texture, upper and lower surfaces.*—Pubescent.

*Venation pattern.*—Pinnate; reticulate.

*Color.*—Developing foliage, upper surface: 137A. Developing foliage, lower surface: 137C. Fully expanded foliage, upper surface: 137A; venation, 137A. Fully expanded foliage, lower surface: 138B; venation, 139D.

*Petiole.*—Length: About 20 cm to 26 cm. Diameter: About 2 mm to 3 mm. Texture, upper and lower surfaces: Canescent. Color, upper and lower surfaces: 146C.

Flower description:

*Flower arrangement and habit.*—Large salverform flowers arranged in long terminal panicles. Freely flowering habit with usually about 20 to 40 open flowers and flower buds per lateral branch at a time. Flowers not persistent. Flowers face mostly outwardly. Flowers not fragrant.

*Natural flowering season.*—Plants of the new *Campsis* flower from late May to September in South Carolina.

*Flower longevity.*—Individual flowers last about six to eight days on the plant.

*Inflorescence height.*—About 20 cm to 30 cm.

*Inflorescence diameter.*—About 20 cm.

*Flower diameter.*—About 7.5 cm to 9 cm.

*Flower length (height).*—About 7 cm to 8 cm.

*Flower bud.*—Shape: Elongated oblong. Length: About 5 cm to 7 cm. Diameter: About 1.4 cm to 1.8 cm. Color: 44C.

*Corolla.*—Arrangement: Five petals fused at the base and opening into a flared trumpet. Petal length from throat: About 2.5 cm to 3 cm. Petal width: About 3 cm to 3.5 cm. Petal shape: Orbicular to elliptic. Petal apex: Obtuse to emarginate. Petal margin: Entire to crenulate. Petal texture, upper and lower surfaces: Smooth, velvety. Color: Petal, when opening, upper surface: 53D. Petal, when opening, lower surface: 51C. Petal, fully opened, upper surface: 53B; color becoming closer to 53A with development. Petal, fully opened, lower surface: 42B.

*Calyx.*—Arrangement: One star-shaped calyx tube with five sepals fused at the base. Sepal length: About 2 cm to 3 cm. Sepal width: About 6 mm to 8 mm. Sepal shape: Lanceolate. Sepal apex: Aristate. Sepal margin: Entire. Sepal texture, upper and lower surfaces: Puberulent. Color, upper surface: 22B. Color, lower surface: 180B.

*Peduncles.*—Length: About 2.5 cm to 4 cm. Diameter: About 3 mm to 4 mm. Angle: About 30° to 45° from vertical. Strength: Strong. Texture: Canescent. Color: 144C.

*Pedicels.*—Length: About 5 mm to 10 mm. Diameter: About 2 mm to 3 mm. Angle: About 30° to 45° from vertical. Strength: Strong. Texture: Canescent. Color: 144C.

*Reproductive organs.*—Stamens: Quantity/arrangement: Four per flower. Anther shape: Oblong. Anther length: About 3 mm to 8 mm. Anther color: 150D. Pollen amount: Moderate to scarce. Pollen color: 13D. Pistils: Quantity: One per flower. Pistil length: About 4 cm to 5 cm. Style length: About 3 cm to 4 cm. Style color: About 145D. Stigma shape: Obelliptic. Stigma color: 150D. Ovary color: 150D. Fruit: Quantity per plant: None to rarely one or two per plant. Length: About 4 cm to 10 cm. Diameter: About 8 mm to 12 mm. Texture: Woody; sparsely pubescent. Color: 177B. Seed: Length: About 3.5 mm to 4 mm. Diameter: About 0.15 mm to 0.2 mm. Color: 166C.

Garden performance: Plants of the new *Campsis* have exhibited good tolerance to rain and wind and have been observed to tolerate temperatures from about −22° C. to about 45° C.

Pathogen/pest resistance: Plants of the new *Campsis* have not been observed to be resistant to pests and pathogens common to *Campsis*.

It is claimed:

1. A new and distinct *Campsis* plant named 'HOMR' as illustrated and described.

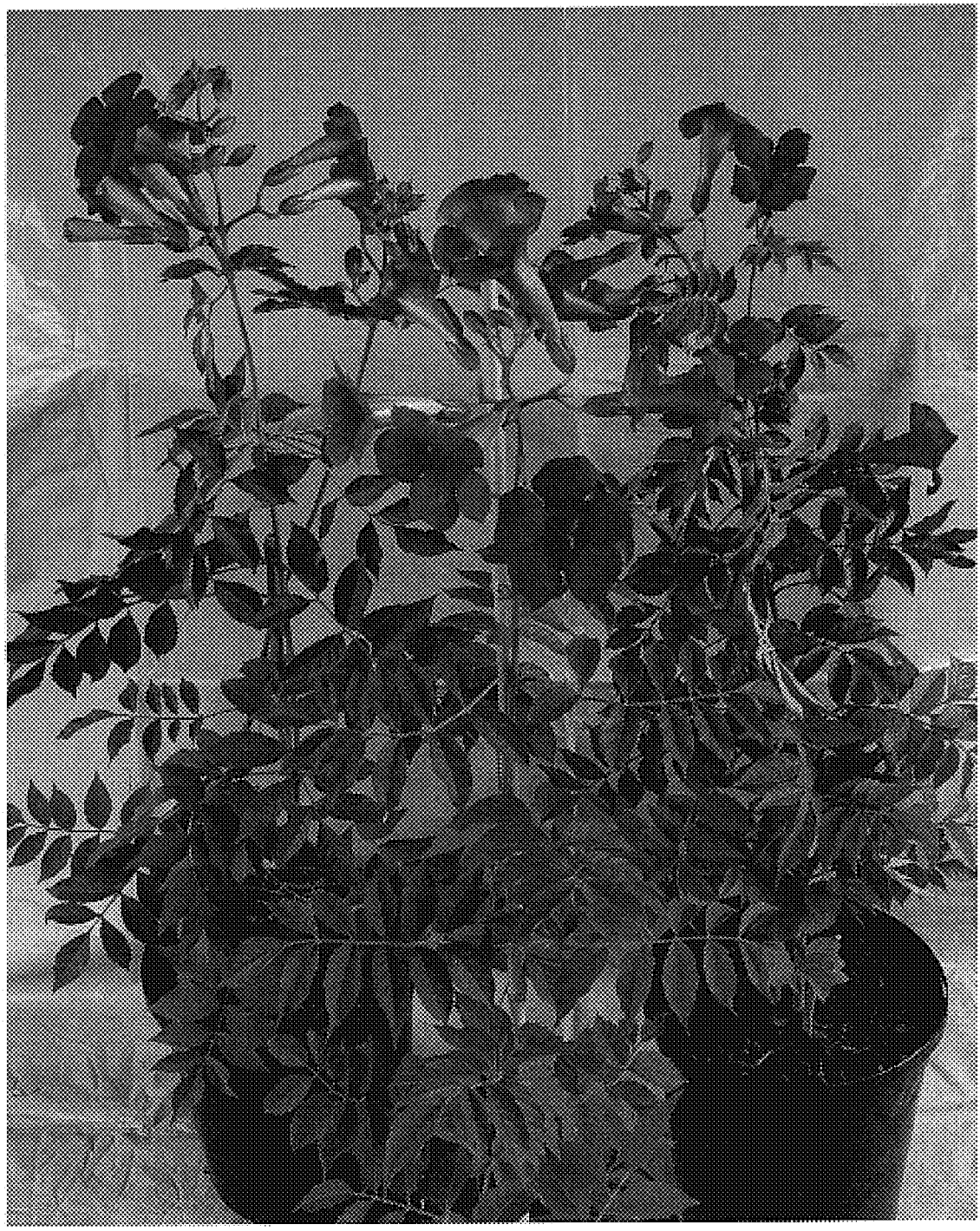

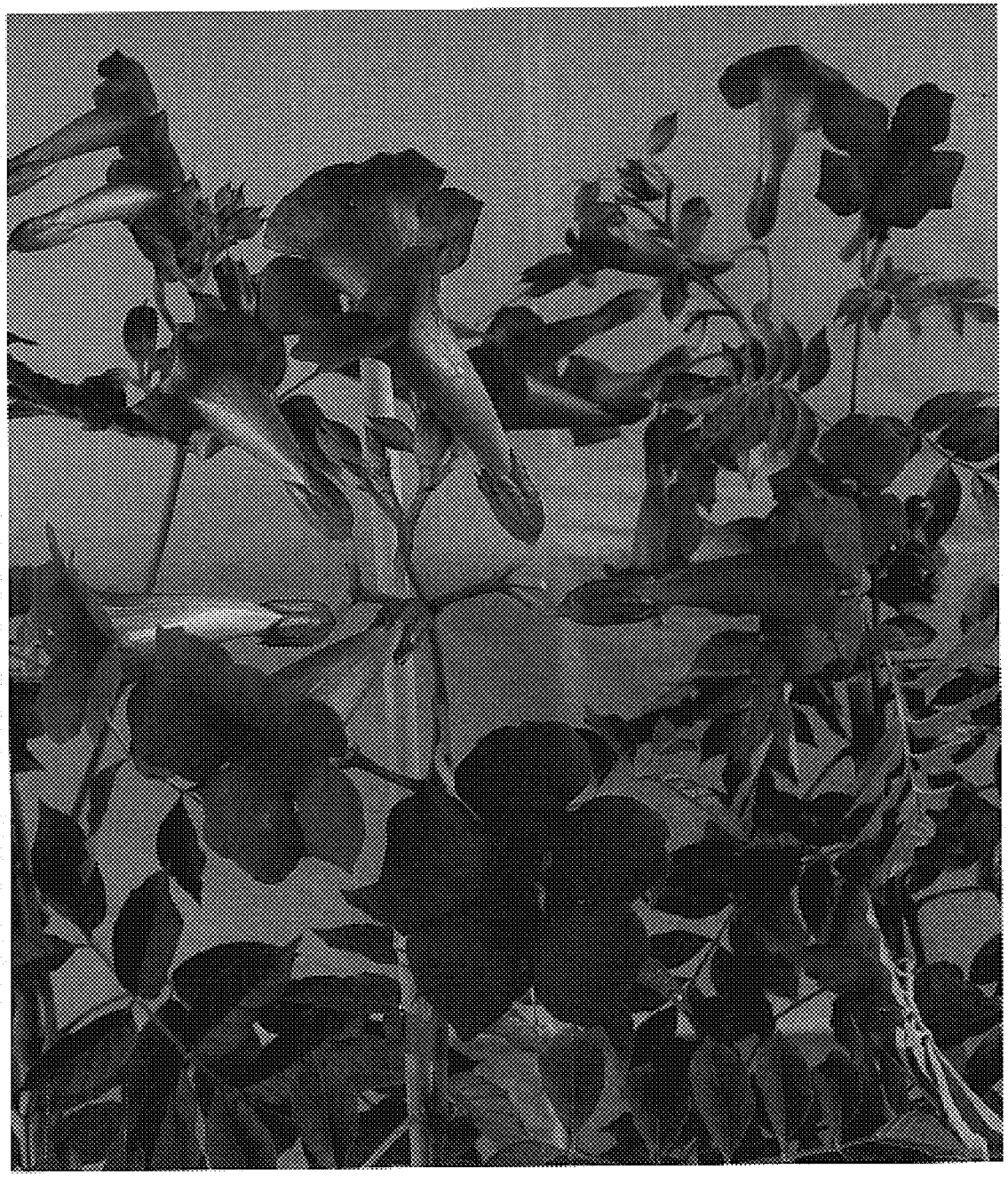

* * * * *